United States Patent [19]
deJong et al.

[11] 4,063,822
[45] Dec. 20, 1977

[54] SYSTEM FOR DETECTING A FIRST LIGHT TRANSMISSIVE SUBSTANCE, SUCH AS FOR INSTANCE BLOOD, IN A SECOND LIGHT TRANSMISSIVE, DIFFERENT SUBSTANCE

[75] Inventors: Leendert Pieter deJong, Reeuwijk; Jan Davidse, Rotterdam, both of Netherlands

[73] Assignee: Staalkat B.V., Aalten, Netherlands

[21] Appl. No.: 671,140

[22] Filed: Mar. 29, 1976

[30] Foreign Application Priority Data

Apr. 4, 1975 Netherlands .................... 7504011

[51] Int. Cl.² .................... G01J 3/42; G01N 33/08
[52] U.S. Cl. .................... 356/179; 356/53; 356/95; 356/97
[58] Field of Search .................... 356/53, 88, 95–97, 356/179–180, 204–206

[56] References Cited

U.S. PATENT DOCUMENTS

| 3,629,589 | 12/1971 | Gleixner | 356/204 |
| 3,799,672 | 3/1974 | Vurek | 356/88 |
| 3,813,168 | 5/1974 | Honkawa | 356/97 |
| 3,887,281 | 6/1975 | Kurita et al. | 356/97 |

Primary Examiner—John K. Corbin
Assistant Examiner—Wm. H. Punter
Attorney, Agent, or Firm—Scully, Scott, Murphy & Presser

[57] ABSTRACT

A detection system for automatically detecting a first light transmissive substance in a second and different light transmissive substance. An optical system is arranged for alternately producing light beam flashes of light having a first wavelength and light having a second wavelength to the input of an opto-electric detector. A volume containing the first and the second substance can be selectively positioned at the output side of said optical means in front of the opto-electric detector. The opto-electric detector delivers its electrical signals corresponding to the light beam flashes received thereby, to a electrical detecting arrangement. The electrical detecting arrangement comprises first means for producing a first voltage proportional to the ratio between light transmitted through the volume under inspection at the first wavelength and light transmitted through the volume under inspection at the second wavelength, and second means for producing a second voltage indicative of a threshold level. A comparator for comparing said first and second voltages then yields an output signal indicative of the ratio between the transmission through the volume under inspection at said first wavelength and the transmission through the volume under inspection at said second wavelength, wherein it is determined whether or not said ratio exceeds the detection threshold level.

10 Claims, 16 Drawing Figures

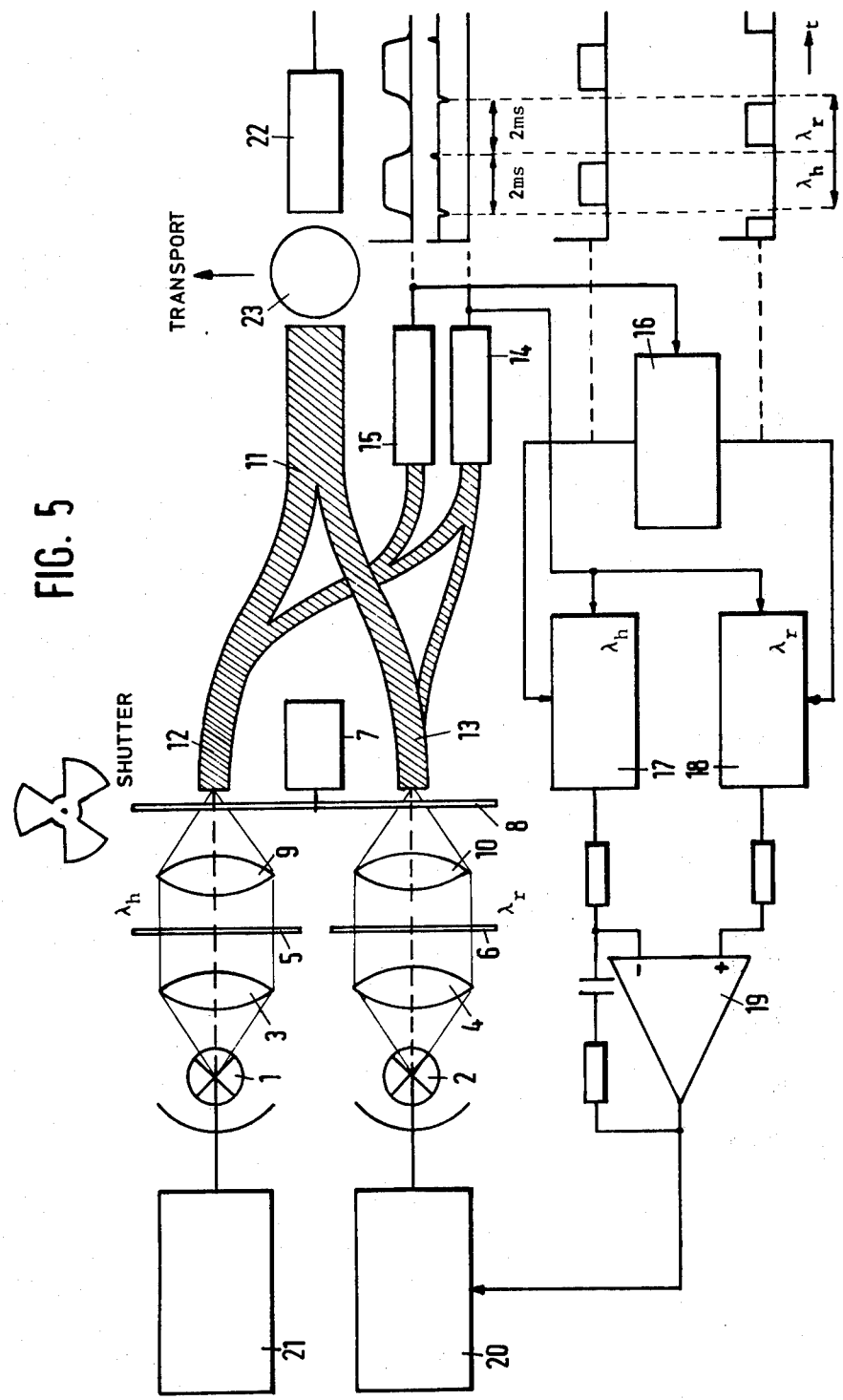

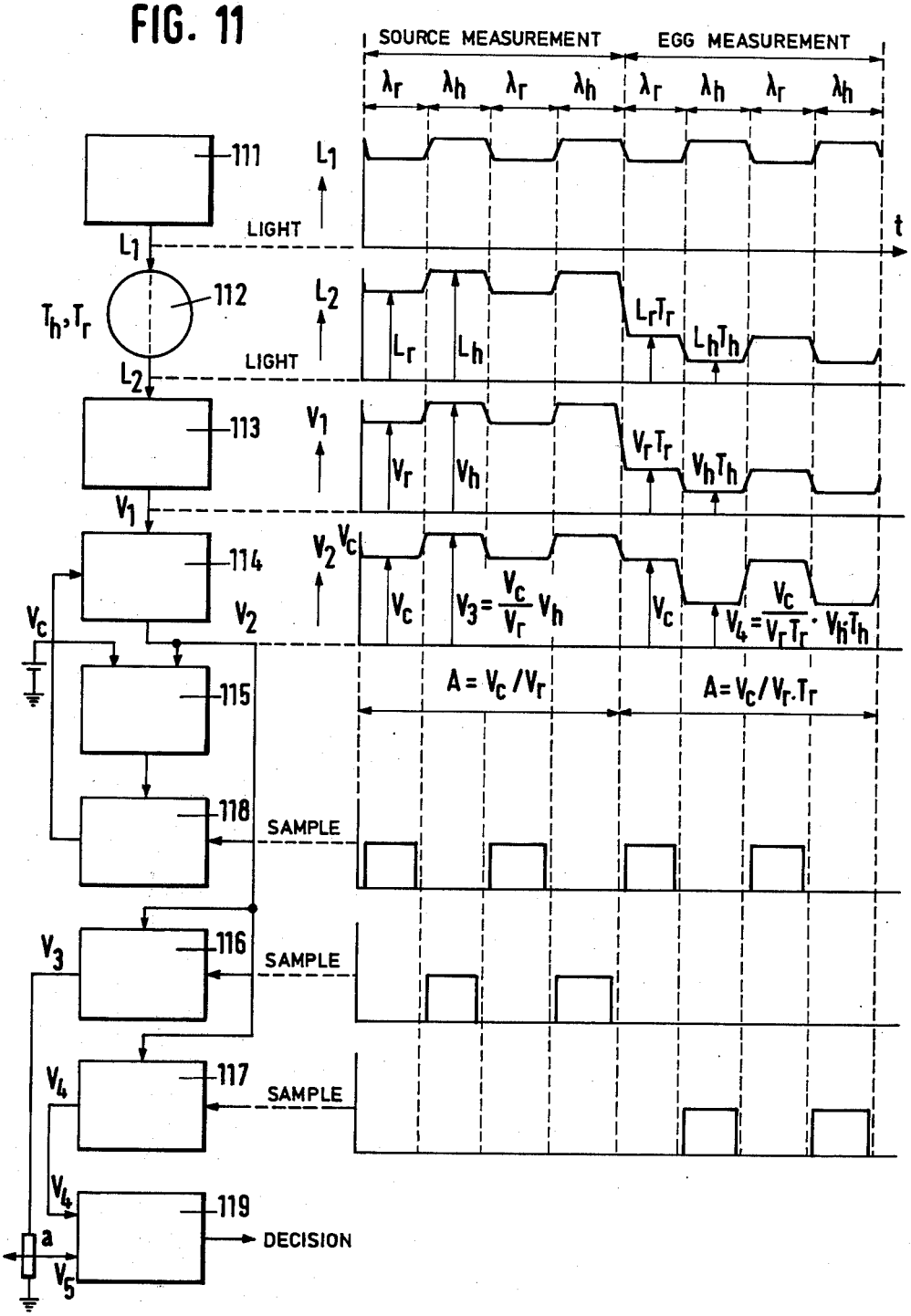

SYSTEM FOR DETECTING A FIRST LIGHT TRANSMISSIVE SUBSTANCE, SUCH AS FOR INSTANCE BLOOD, IN A SECOND LIGHT TRANSMISSIVE, DIFFERENT SUBSTANCE

The invention relates to a system for detecting a first light transmissive substance, such as for instance blood, in a second light transmissive, different substance.

More in particular the invention relates to a system for inspecting or candling eggs, for determining whether an egg under inspection contains blood and has to be rejected. Although not restricted to such egg inspecting systems, the invention in the following will be described and illustrated with reference to such egg inspecting systems, in other words automatic egg candling systems involving the elimination of eggs known to be to the trade as "bloods".

Such a system is for instance disclosed in U.S. Pat. No. 2,823,800, patented Feb. 18, 1958 in the name of George N. Bliss, and titled "Automatic candler for brown or white eggs."

According to this prior art alternate beams of light of various wavelengths are transmitted to an egg under inspection. The one beam contains light of a wavelength which is not selectively absorbed by blood, i.e. a reference wavelength $\lambda$, while the other beam contains light of a different wavelength which is slectively absorbed by blood (hemoglobin), i.e. a measuring wavelength $\lambda_h$. These beams are alternately received by a photosensitive detector device which in response to the alternate light beam flashes applied thereto produces corresponding electrical voltages indicative of the transmissions of light passed through the egg under inspection. These voltages are processed in an electric detection arrangement which is adapted to produce a reject signal if light to a certain extent is absorbed by hemoglobin present in an egg under inspection. Actually a first voltage proportional to the light from the first beam transmitted by the egg is compared with a second voltage proportional to light from the second beam transmitted by the same egg. Consequently the absolute difference between these two voltages provides a criterion for rejecting an egg "(blood)". To initially set this known system, an egg known to be free from blood is placed in the path of said light beams, and the voltages on either the one or the other light is adjusted so that these voltages are cancelled. Now due to the fact that the level of transmissibility for different eggs of a run to be candled by the system can vary of a wide range of values, this known system is not optimum. For instance if the system is set for light eggs, dark (brown) eggs can be falsely rejected, while if the system is set for dark (brown) eggs, white eggs can be falsely rejected.

Now it is a main object of the present invention to improve the detection of a first light transmission substance, such as for instance blood, present in a second light transmissive and different substance. More in particular it is an object of the object invention to overcome the deficiencies inherent to the prior art, so as to optimize the detection with substantial exclusion of false rejects. Further it is an object to provide a reliable, time stable detection which is suitable for use in combination with a conveying system wherein the eggs to be inspected are conveyed, for instance with a speed of one egg per second, without necessity of time-consuming and cumbersome adjusting procedures.

The detection system according to the subject invention comprises an optical system for producing and directing respectively said first light beam and said second light beam as well along the same optical axis; support means for supporting an egg for inspection in such a manner that light from said first light beam and light from said second light beam as well is transmitted along said optical axis and through said egg; a photosensitive detector for producing a first voltage proportional to light transmitted to the egg under inspection at the measuring wavelength $\lambda_h$, and producing a second voltage proportional to light transmitted through the egg under inspection at the reference wavelength $\lambda_r$; an electric detector arrangement being adapted to determine whether or not a ratio derived from said first voltage and said second voltage and indicative of the transmission through said egg at $\lambda_h$ relative to the transmission through said egg at $\lambda_r$ exceeds a predetermined threshold level. In order to cover the wide range of levels of transmissibility for the different eggs of a run to be candled, for instance a dynamic range of $10^3$ is practically feasible, the electric detection arrangement comprises a controlled gain amplifier with an associated control arrangement by means of which the output signal from said amplifier each time a voltage proportional to light with said reference wavelength $\lambda_r$ is produced, is adjusted at a constant value which has the effect that the output signal produced each time when a voltage proportional to light transmitted with the measuring wavelength $\lambda_h$ through the egg under inspection is applied, by its magnitude then is indicative of the desired ratio between voltages proportional to light transmitted through the egg under inspection at wavelength $\lambda_h$ and $\lambda_r$ resp. an embodiment illustrative of the subject invention comprises variable light source means for producing light at said reference wavelength, said variable light source means being included in a servo loop circuit for controlling the light output $L_r$ provided by said optical system, to sustain a constant ratio $L_h/L_r$, wherein $L_h$ is the stabilized light output of the light source providing light containing said measuring wavelength $\lambda_h$.

Now it is assumed that the light output of each of said light beams at the output side of said optical system is $L_r$ (reference) and $L_h$ (hemoglobin) respectively, while the transmission at each of said wavelength $\lambda_r$ and $\lambda_h$ respectively through an egg under inspection is $T_r$ and $T_h$ respectively. The photosensitive detector then will alternately produce signals $V_r$ and $V_h$ respectively proportional to $L_r \cdot T_r$ and $L_h \cdot T_h$ respectively. Consequently the desired ratio $T_h/T_r$ as a criterion for deciding whether or not an egg is acceptable, can be found by measuring $V_h/V_r = L_h T_h/L_r T_r$, while keeping $L_h/L_r$ constant by means of a control arrangement.

The afore-mentioned embodiment offers the possibility to inspect a run of eggs which for instance by means of a conveying system are continuously moved along the inspection location, where the light beams are transmitted through an egg under inspection, without the necessity to remove an egg from the conveyor and place such egg in the light beam path. However, the requirement to control the light source producing the light beam with the reference wavelength has following deficiencies. Firstly, a second photosensitive detector for deriving control information for regulating the light output of the light source for the reference wavelength, is not located at the output end of said optical system where light is transmitted through the egg under inspection. Consequently, variations in the transfer characteristics of the optical path following the location where the light for said second photosensitive detector is branched-off, will detrementally affect the ultimate measurement of the ratio $T_h/T_r$. Secondly in a candling system wherein the eggs to be inspected are supplied for instance by means of 12 parallelly running conveyors, 12 servo system for control of 12 optical systems would be required, which means a cumbersome and expensive solution.

Now in another embodiment illustrative of the subject invention these drawbacks of the afore-mentioned embodiment can be overcome. In this other embodiment a conveyor system is advantageously employed, wherein each egg for inspection is lifted-off the conveyor and held sufficiently long, for instance 300 msec. in the light beam path for performing an "egg measurement" of the ratio $T_h/T_r$ thereby that alternate light beam flashes $L_r \cdot T_r$ and $L_h \cdot T_h$ respectively are applied through the egg under inspection to the photosensitive detector; during the intermediate interval between successive lift-offs and in the absence off an egg positioned in front of said detector, a "light source measurement" is then performed, wherein to that same detector alternate ligh beam flashes $L_r$ and $L_h$ respectively are applied. Now the voltages $V_r$ and $V_h$ respectively alternately produced by said photosensitive detector in response to the light beam flashes $L_r$ and $L_h$ applied thereto, and the voltages $V_r \cdot T_r$ and $V_h \cdot T_h$ alternately produced by said photosensitive detector in response to light beam flashes $L_r \cdot T_r$ and $L_h \cdot T_h$ respectively applied thereto during an "egg measurement", are processed in an electric detector arrangement in such a manner that from these four voltages of which $V_r$ and $V_h$ are produced alternately during a "light source measurement interval", and $V_r \cdot T_r$ and $V_h \cdot T_h$ are alternately produced during an "egg measurement interval", it is determined whether or not the ratio $T_h/T_r$ exceeds a preset detection threshold level.

This is achieved thereby that a first voltage derived during an "egg measurement interval" from light beam flashes at the measuring wavelength $\lambda_h$, as $$V_C \cdot \frac{V_h \cdot T_h}{V_r \cdot T_r},$$

wherein $V_C$ is a constant reference voltage, is compared with a second voltage derived during a "light source measurement interval" from light beam flashes at the measuring wavelength $\lambda_h$, as $$a \cdot V_C \cdot \frac{V_h}{V_r},$$

wherein $a$ is representing said detection threshold level. With this other embodiment also a controllable gain amplifier is employed to cover the dynamic range of the transmissibility for the eggs to be inspected. The gain of the amplifier is controlled in such a manner that the output signal thereof during the occurrence of light beam flashes at the reference wavelength $\lambda_r$ is regulated at a constant value $V_C = A \cdot V_r$, wherein $A$ the gain of the amplifier and $V_r$ a voltage proportional to the light applied during the source measurement interval at the wavelength $\lambda_r$, while during an egg measurement interval the amplifier output signal also is regulated at said constant value $V_C = A \cdot V_r \cdot T_r$. If the result from the above comparison yields the first voltage exceeds said second voltage, in other words $$V_C \cdot \frac{V_h \cdot T_h}{V_r \cdot T_r} > a \cdot V_C \frac{V_h}{V_r}$$

or in other words the desired ratio $T_h/T_r > a$, the egg under inspection is approved, while in the opposite case, wherein $T_h/T_r < a$, the respective egg is rejected as a "blood-egg".

Before describing the present invention with reference to two embodiments, the spectral properties of eggs will be discussed in some detail as it is essential for an achievement of the objects contemplated that the optical spectrum analysis of the light emanating from the respective side of the egg and collected from a portion of the egg surface is optimal.

Figure 4A:
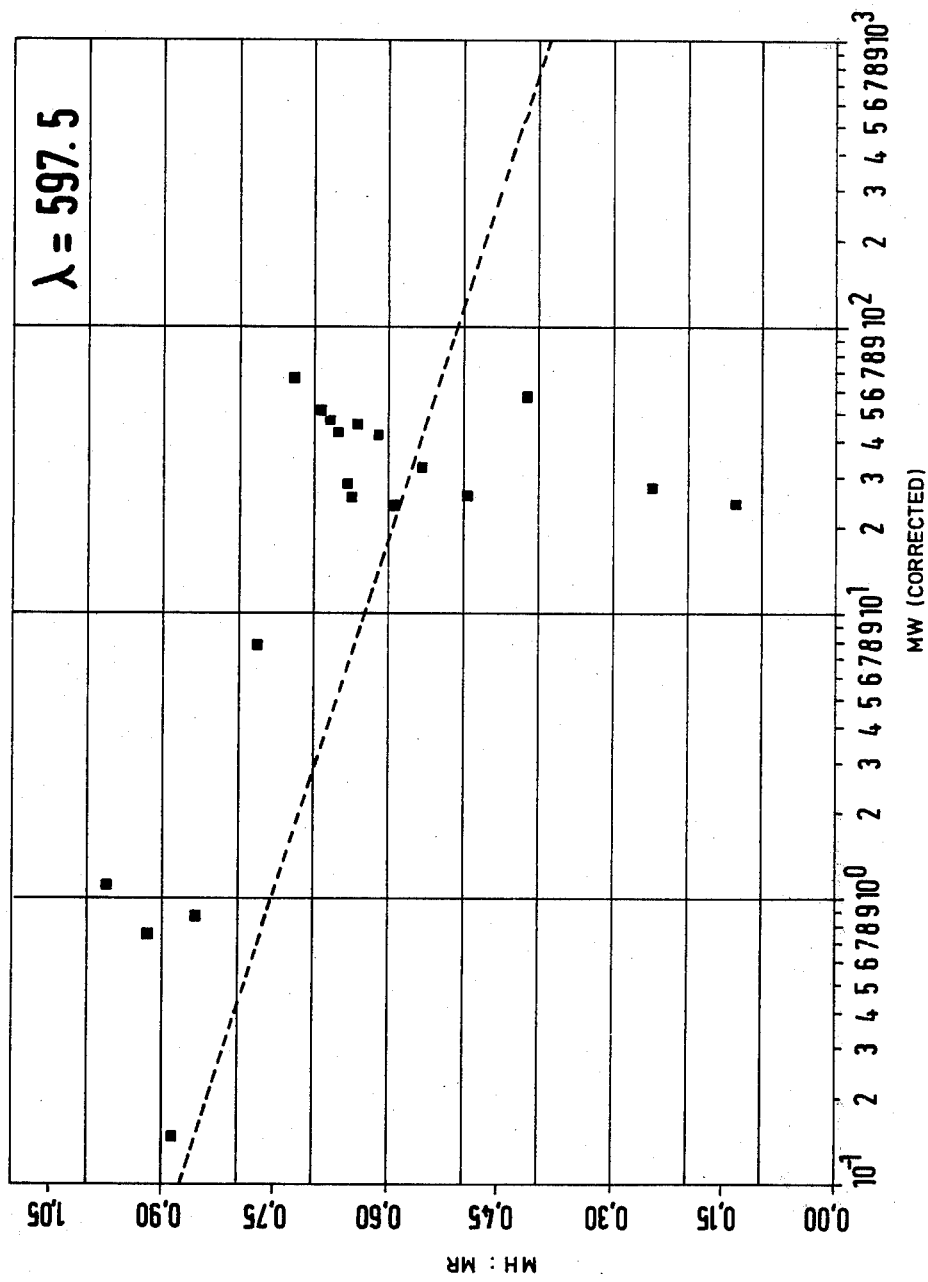
Figure 4B:
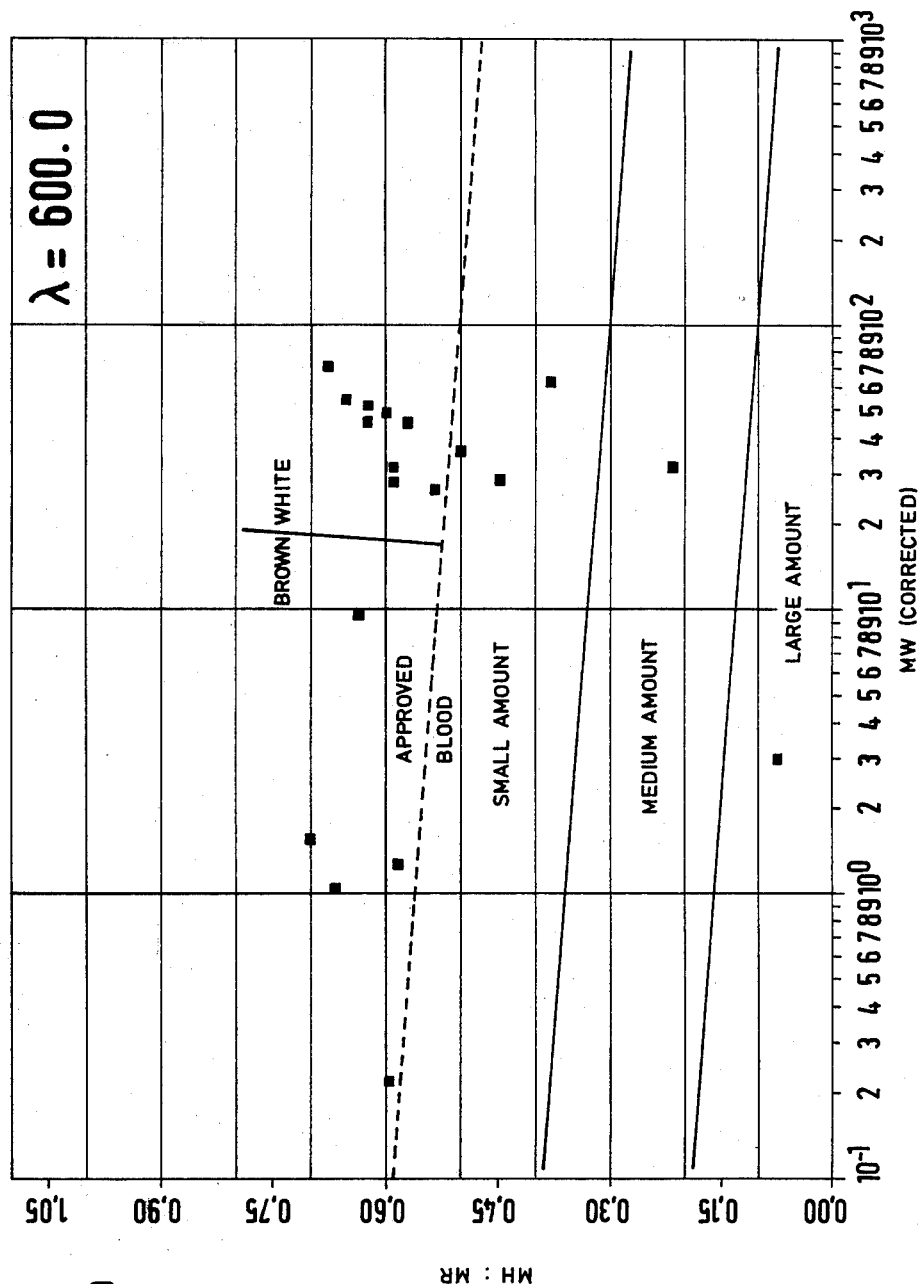
Figure 4C:
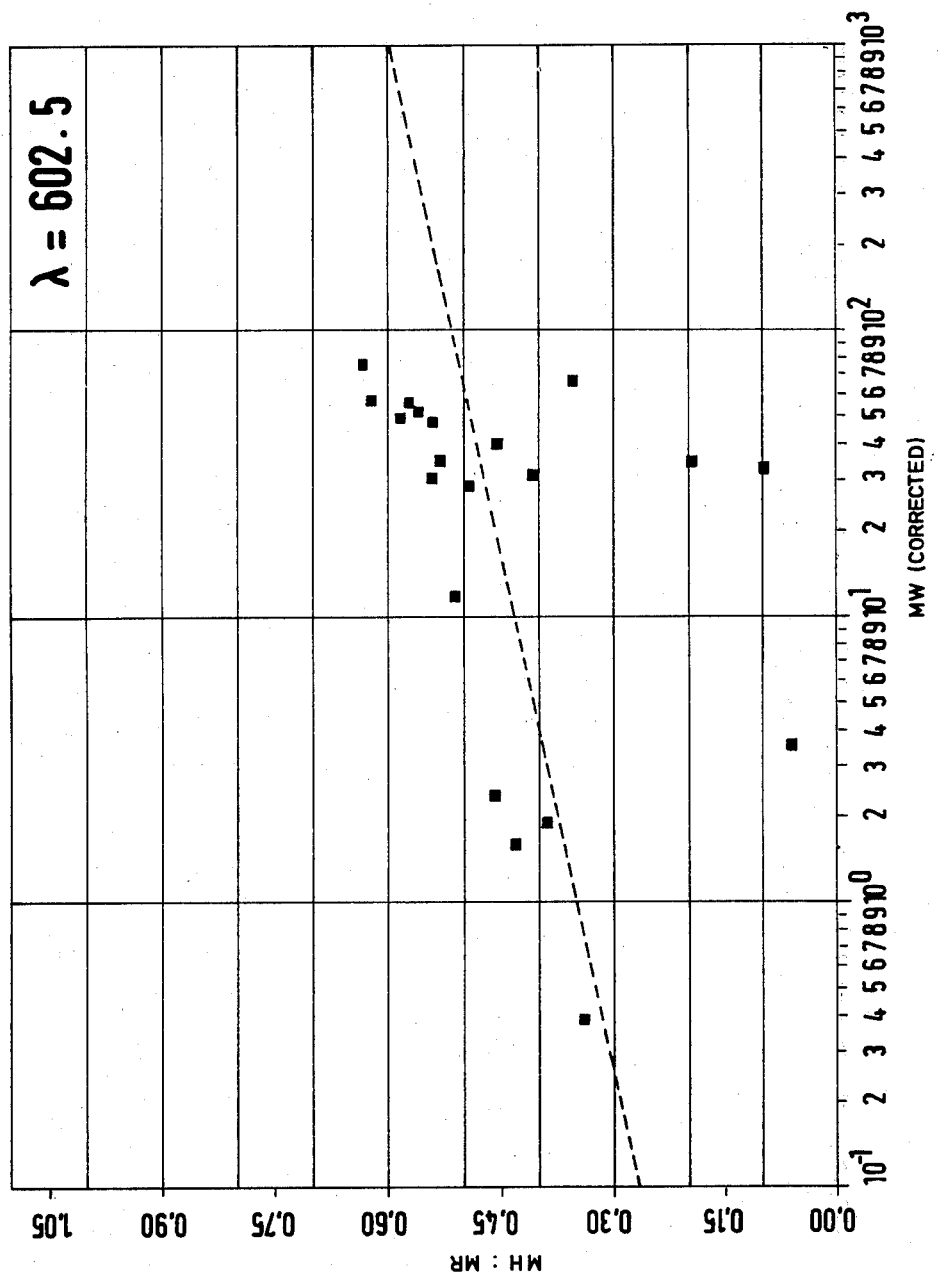

FIGS. 4a, 4b, and 4c are graphs of the associated measuring values (MW corrected) and transmission ratio values (MH/MR) for a number of different reference wavelengths.

FIG. 5 shows an electro-optical arrangement having two light sources, associated lens systems, and servo loop circuits for controlling the light output.

Figure 6:
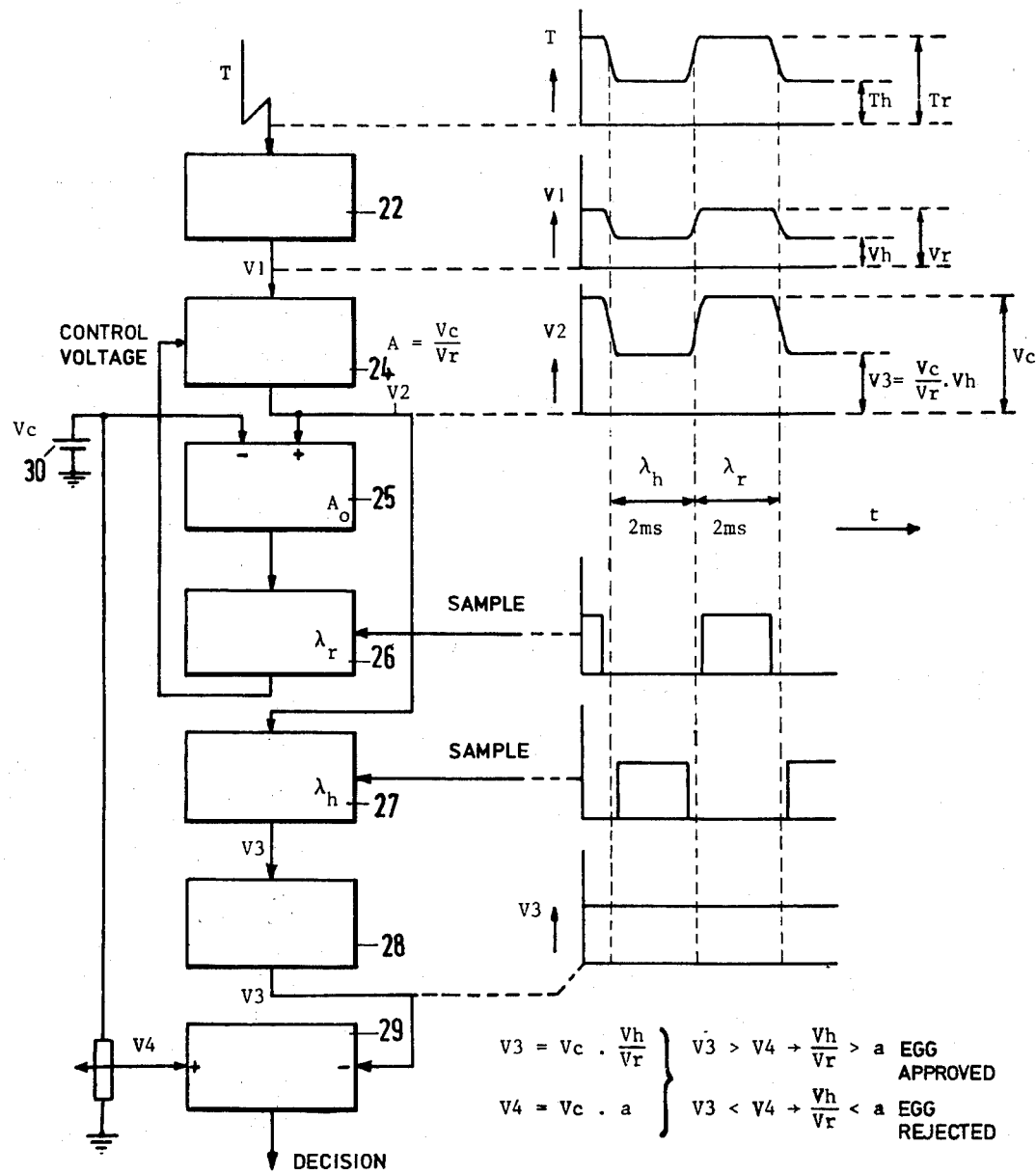

FIG. 6 is a block diagram of an electronic detection system for determining the ratio between transmissions at wavelengths $\lambda_h$ and $\lambda_r$.

Figure 7:
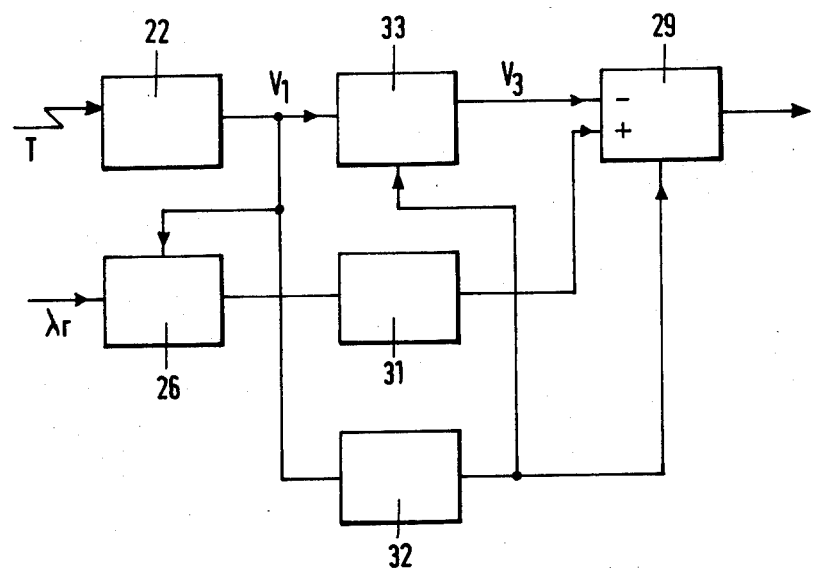

FIG. 7 illustrates a circuit for controlling detection thresholds as a function of the transmission at wavelength $\lambda_r$.

Figure 8:
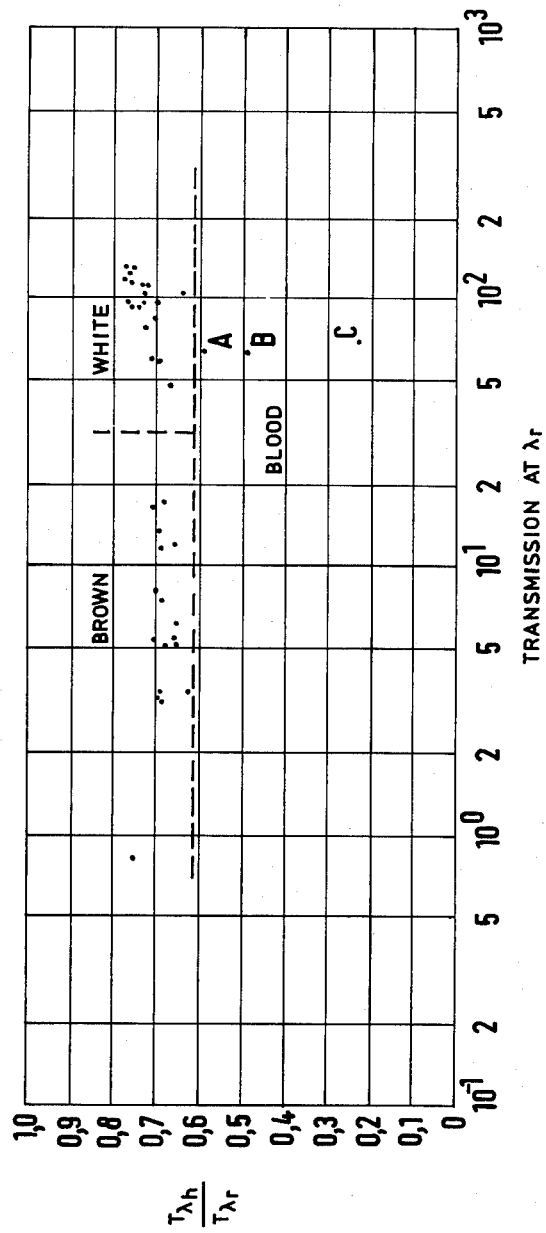

FIG. 8 illustrates measurement results obtained by the present invention on a number of brown and white eggs.

Figure 9A:
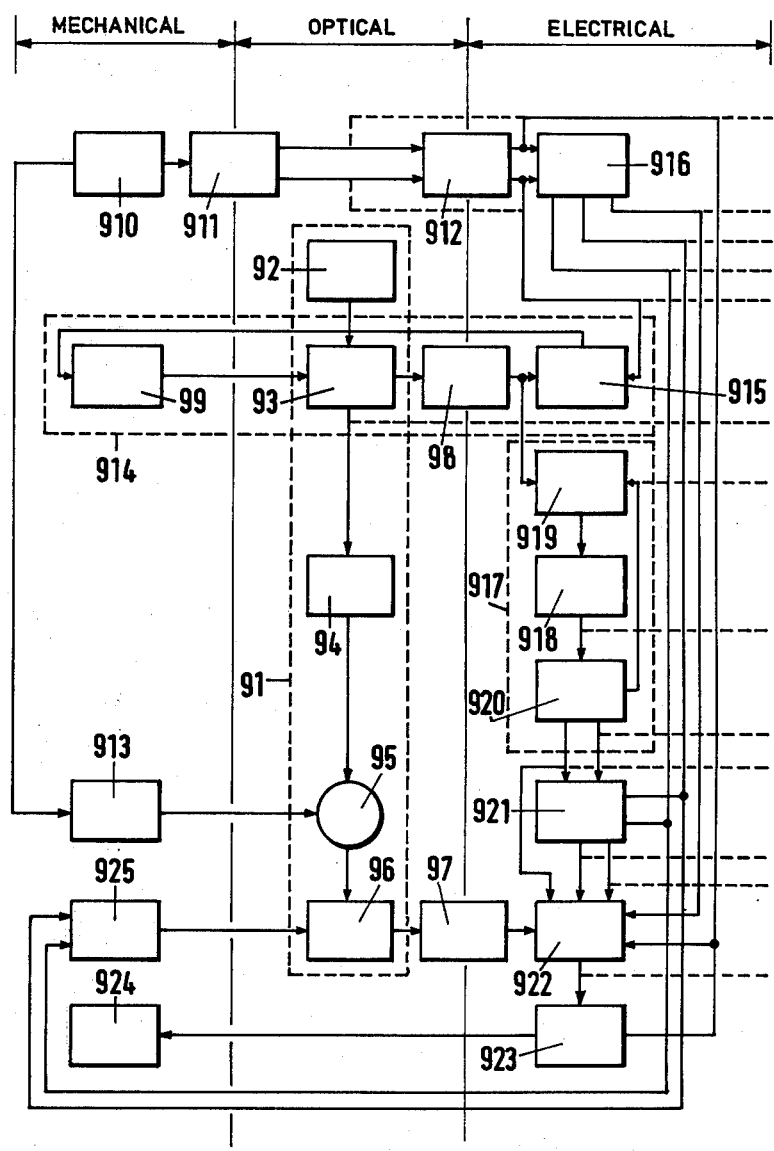
Figure 9B:
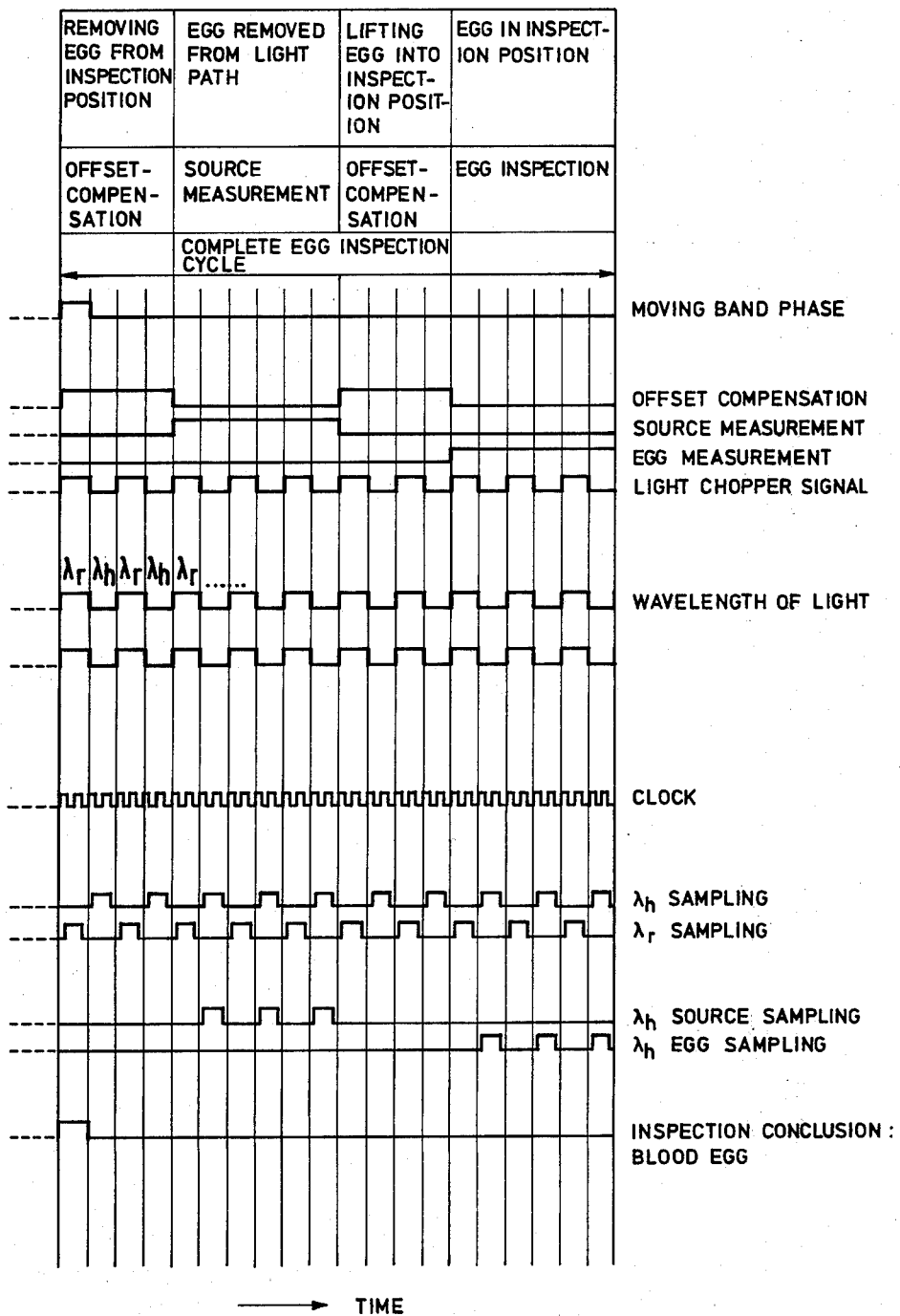

FIGS. 9a and 9b show respectively another embodiment of an automatic egg candling system, and different wave forms generated therein.

Figure 10A:
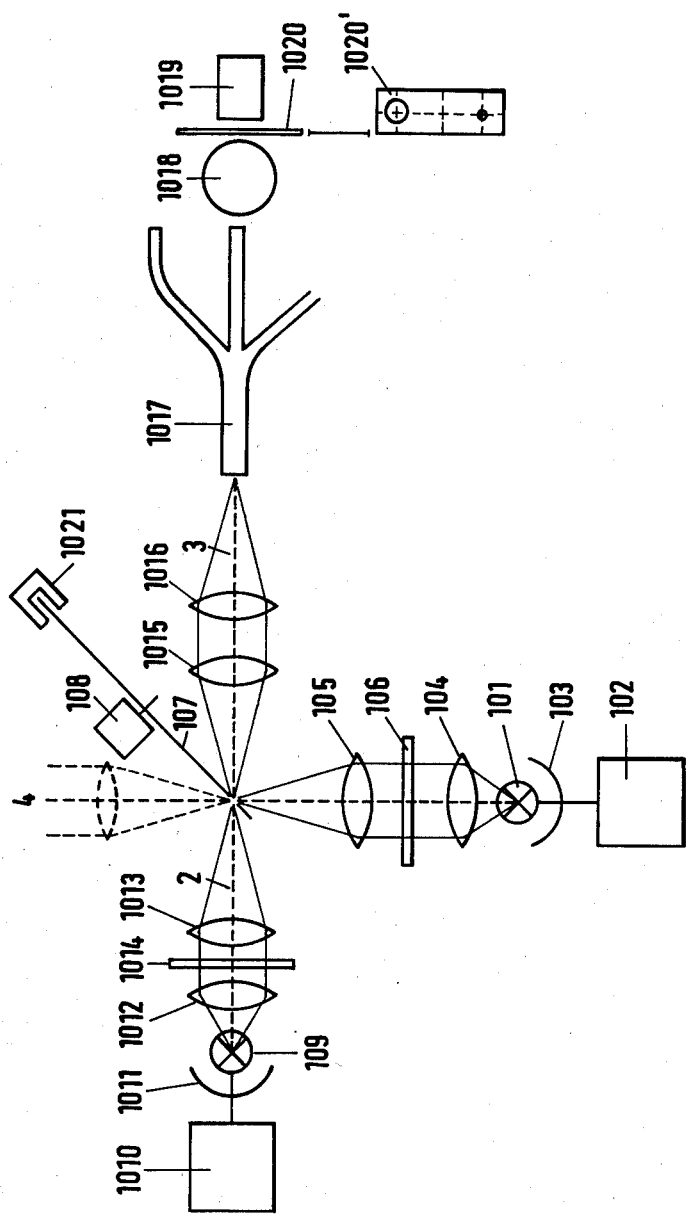

FIGS. 10a, 10b, and 10c illustrate respectively an optical system which may be utilized in the automatic egg candling system, wave forms formed in the optical system, and details of a chopper disc employed in the system.

FIG. 11 is a block diagram of an electrical detection arrangement and wave forms generated therein.

Figure 1:
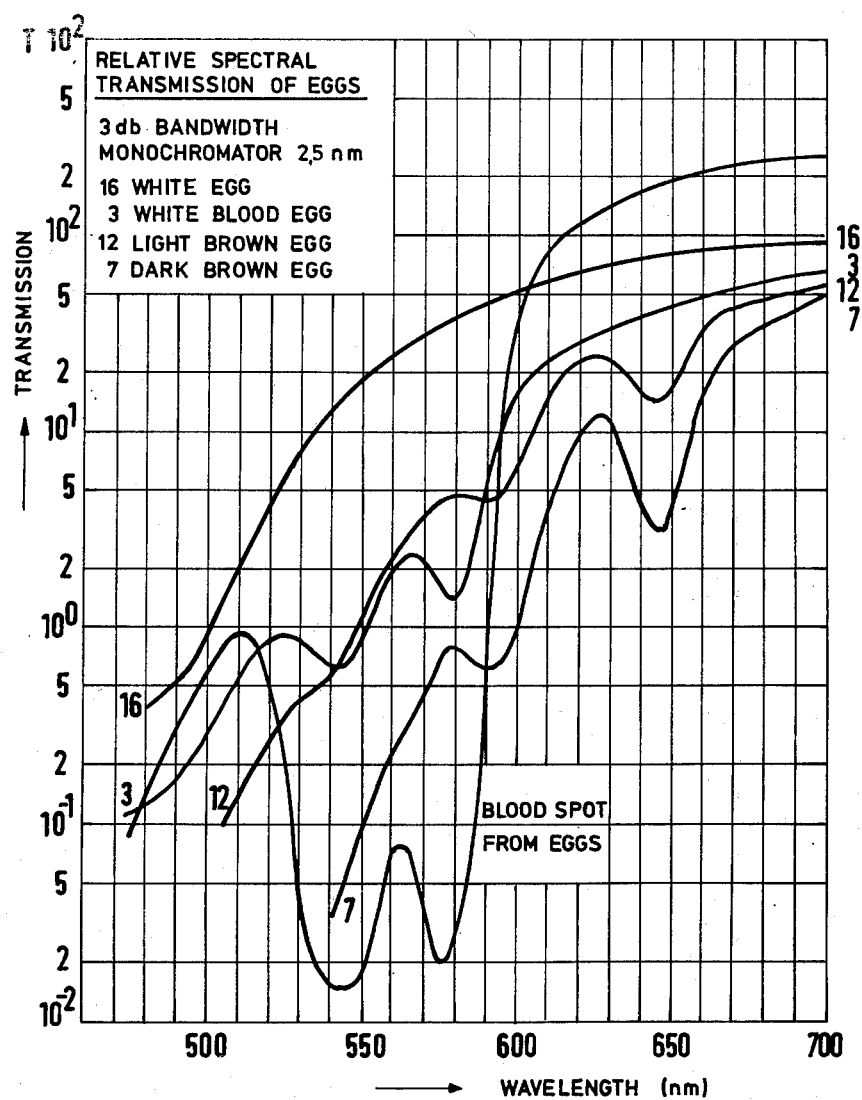
FIG. 1 is a graph of the transmission characteristics of different eggs as a function of the wavelength of the radiating light.

In order to be able to ascertain the manner in which an optical spectrum analysis is to be performed, the spectral transmission has been determined of a plurality of eggs of highly dissimilar contents and outward appearance. By way of example, FIG. 1 shows the transmission for different eggs as a function of the wavelength of the light with which the respective egg is irradiated. White eggs, such as 16, exhibit a gradually decreasing transmission towards shorter wavelengths, mainly caused by the yolk. Brown eggs, such as 12 and 7, exhibit clear absorption peaks at $\lambda \approx 590$ and $\lambda \approx 645$ nm as a result of pigments in the shell, while at shorter wavelengths the transmission may be more than a factor 100 smaller than that of white eggs. As may be expected in view of the absorption spectrum of hemoglobin, blood eggs, such as 3, have relative transmission minimums at $\lambda = 576$ and $\lambda = 542$ nm. By way of illustration, FIG. 1 further shows the transmission of an isolated blood spot. It is a striking fact that at, for example $\lambda = 576$ nm blood spots cause a relative absorption which is far higher than the relative volume or surface area of the spot with respect to the whole egg. Compare, for example, egg 3 containing a blood spot of $\simeq 30$ mm² to egg 16. The internal dispersion at the egg shell causes a weak red luminescence of the entire egg due to the presence of a blood spot.

It further appears that blood eggs have a far lower transmission throughout a large part of the spectrum than comparable blood-free eggs (for example, compare again eggs 3 and 16). As a result thereof, in a batch of eggs the ratio between the lowest and the highest transmission measured in certain wavelength ranges (i.e. the dynamic range) can be as high as 1 : 1000. For normal white eggs the transmission at $\lambda = 542$ nm is approximately 2.5 times less than at $\lambda = 576$ nm, mainly due to the yolk. For light brown eggs this factor may be as high as 10 and for dark-brown eggs even as high as 20. For these eggs, consequently, when $\lambda = 542$ nm the masking of the hemoglobin absorption maximum is so complete that only a measurement at $\lambda = 576$ nm is suitable for blood detection.

Figure 2:
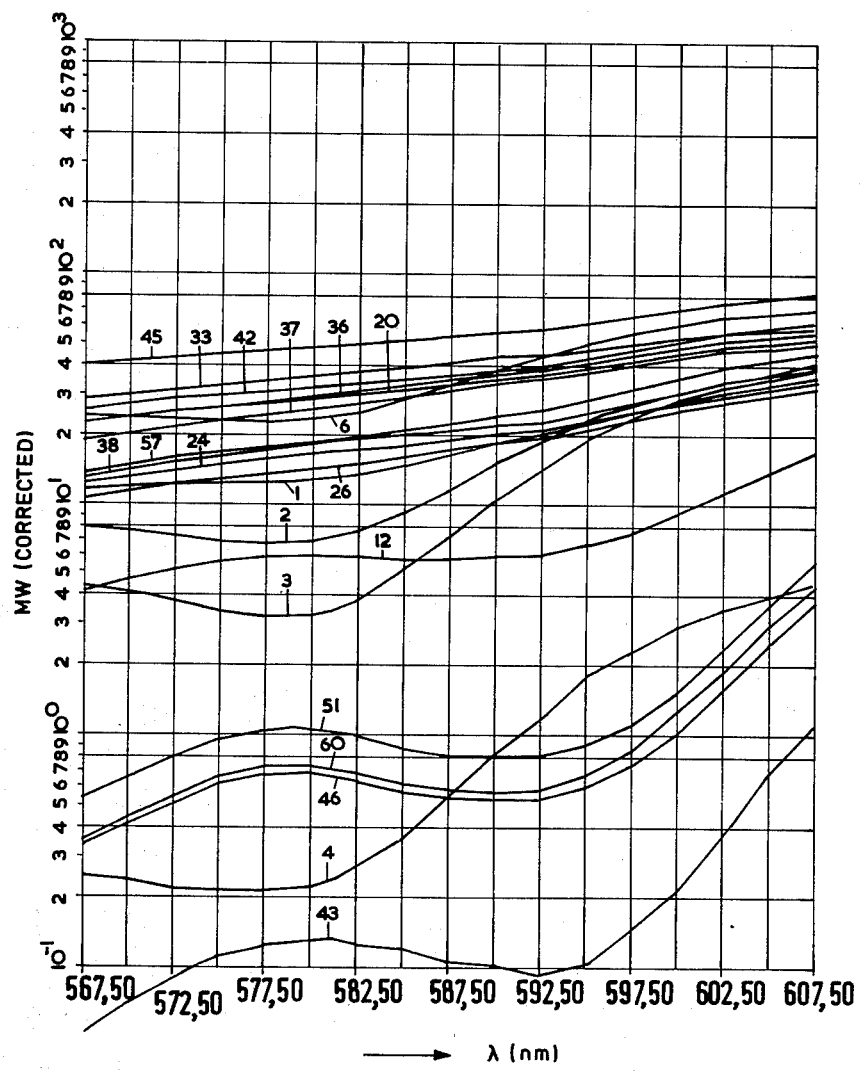
FIG. 2 shows the measuring values MW of 20 different eggs as a function of wavelength.

As only a relatively small spectral range is suitable for blood spot detection, FIG. 2 shows the transmission as a function of the wavelength of the light used for irradiating 20 selected eggs. A measuring value MW, which is representative of the transmission an has been corrected for the transmission properties of the measuring system, is plotted on the ordinate. The group of 20 eggs has been selected from a batch of 60 eggs collected by a candling station during 2 weeks, and includes the most transparent and the most dark eggs. In addition, eggs containing much blood and a number of doubtful cases have been included in this group.

It will be clear that an absolute transmission measurement at $\lambda_h = 576$ nm is in sufficient for the detection of blood in eggs due to the strong influence of other properties of the egg, such as the thickness of the shell, the colour of this shell and the colour of the yolk. Ideally, it should be possible to compare each blood egg to an identical egg containing no blood, so that the influence of all the properties of the egg, except for the presence of blood, could be eliminated. This ideal situation might be approximated if a reference measurement could be performed to each egg, the result of which measurement would depend on the same properties of the egg as that of the measurement at $\lambda_h = 576$ nm but is not or hardly affected by the presence of blood in this egg. The egg would, in a manner of speaking, be compared to itself in its more perfect form.

This reference measurement should be performed at a wavelength $\lambda_r$ which is sufficiently remote from the measuring wavelength $\lambda_h$ to eliminate the influence of blood that may be present, but at the same time is sufficiently near to this measuring wavelength so as to have the influence of the other properties of the eggs at the two wavelengths correspond optimally. Moreover, the reference wavelength $\lambda_r$ must not be smaller than $\lambda_h$ in view of the highly increasing attenuation in this part of the spectrum.

Figure 3:
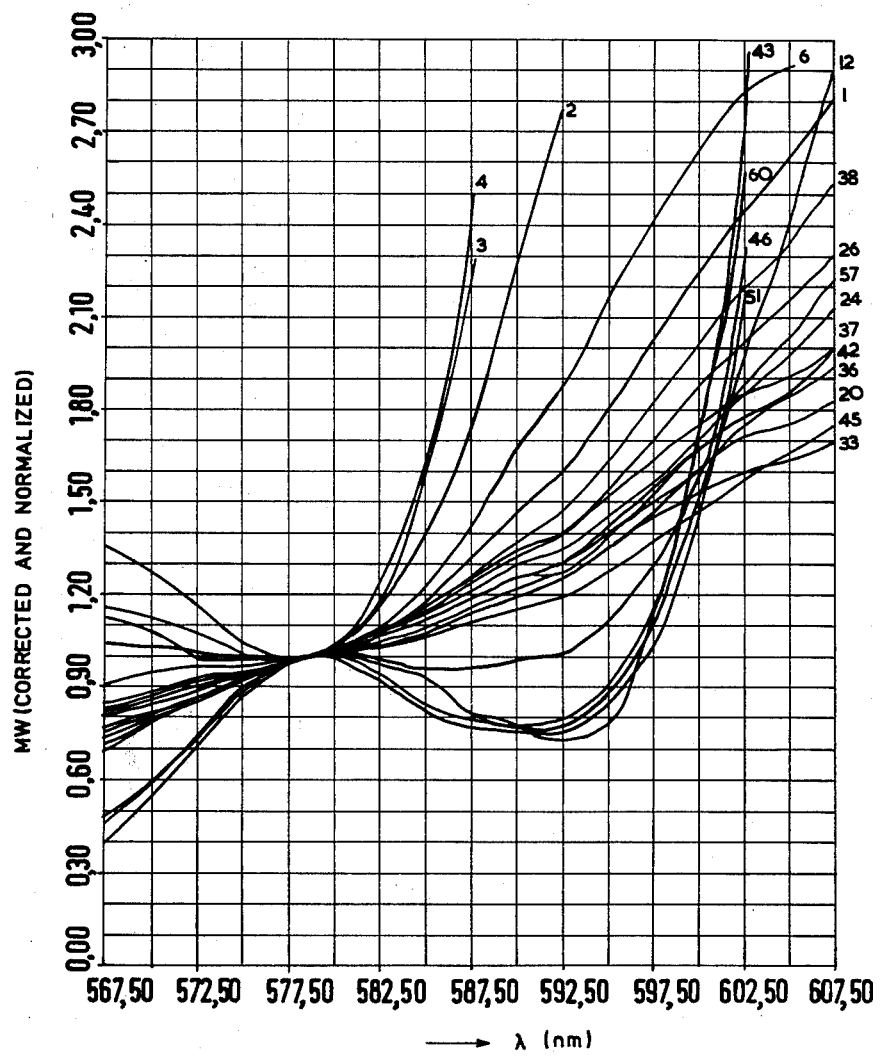
FIG. 3 illustrates the spectral transmission of the same 20 eggs normalized with respect to the measuring wavelengths.

In order to gain an insight in the possibilities concerning the choice of a suitable reference wavelength $\lambda_r$, in FIG. 3 there is shown the spectral transmission of the same selected group of 20 eggs, through now normalized with respect to the measuring wavelength $\lambda_h$.

It clearly appears that there is a wavelength range around 600 nm within which the relative transmission as compared to that at $\lambda_n$ lies within certain limits ($\pm$ 1.6) for all good eggs, irrespective of the kind of egg.

At wavelength $\lambda \simeq 600$ nm blood eggs have a relative transmission that is greater than 1,6 and increases as a greater amount of blood is present.

Therefore, the detection criterion is chosen to be the ratio between the transmissions at wavelengths $\lambda_h$ and $\lambda_r$, in which $\lambda_r \simeq 600$ nm.

It appears in practice that there is a spread in the chosen transmission ratio of good eggs which cannot be neglected. Dark-brown eggs stand a good chance of being rejected due to the steepness of the curve representing this ratio in the vicinity of $\lambda_r = 600$ nm (false rejects).

In view thereof, $\lambda_r$ is chosen to be slightly less than 600 nm, resulting in a slight decrease in the sensitivity of the arrangement in so far as the detection of blood in brown eggs is concerned. This has no serious consequences, however, because brown blood eggs are rather rare.

In order to achieve an optimal for the value of $\lambda_r$, the ratios between the transmissions of the same 20 eggs having highly dissimilar properties at wavelengths $\lambda_h$ and $\lambda_r$ ($T\lambda_h/t\lambda_h$) are determined as a function of the transmission at the reference wavelength ($T\lambda_r$). To this end, for a number of $\lambda_r$-values, i.e. 597.5 nm, 600 nm and 602.5 nm as derived from FIGS. 2 and 3, the associated measuring values (MW corrected) and transmission ratio values (MH/MR) for the responsive 20 eggs are determined and plotted as abscissa and ordinate coordinates. This is shown in FIGS. 4a, b and c. It appears that clusters of different types of eggs occur. Good eggs are found in that region above the broken line, blood eggs in the region below this line.

It appears from the measuring results shown that throughout the entire density area the detection sensitivity may be optimized by a dynamic control of the detection threshold in conjunction with the absolute transmission at the reference wavelength. This may also be important if it should appear technically impossible to exactly realize the optimal types of light.

Moreover, knowing the absolute transmission is essential for the detection of old blood eggs which have a transmission ratio resembling that of good eggs but have a considerably lower absolute transmission.

The electro-optical features of the arrangement according to the invention will be discussed hereinafter with reference to FIGS. 5, 6 and 7.

The measuring system employs two types of light, one having a wavelength $\lambda_h \simeq 576$ nm (measuring wavelength) and the other having a wavelength $\lambda_h \simeq 600$ nm (reference wavelength). The following general requirements are imposed on the arrangement.

1. The arrangement must be so that the ratio between the transmissions at these two wavelengths is measured.

2. The absolute transmission of the measuring system must be fixed (inter alia in connection with the control of the detection threshold), preferably for a period of time sufficient to eliminate the necessity of regular recalibration.

3. The measurement of the transmission ratio must be performed with sufficient accuracy throughout a dynamic range of 1 : 1000.

An accurate measurement of the transmission ratio renders it necessary, inter alia, to transmit the two types of light along *the same optical axis*, as it has appeared that the transmission ratio may be affected by a difference in the distribution of the types of light within the egg if light is transmitted through the egg at two different places. To this end, an optical system is chosen in which the two types of light, which originate from two separate sources and are alternately applied to the egg, are guided along the same optical axis by means of fibres; this results in a simple and robust structure. Accurate measurement further requires a stable and accurate ratio between the intensities of the two types of light.

A stable absolute transmission requires a stabilization of the intensities of the two types of light. The use of a *semiconductor photodetector* renders it possible to maintain the total transmission of the measuring system at a sufficiently constant level. A photomultiplier stands at a disadvantage in this respect, leaving out of account the matter of service life and the danger of failure due to excessive light input. In connection with the required sensitivity, however, attention has to be paid to the efficiency of the transmission path.

To permit a measurement of the transmission ratio over a wide dynamic range, the use of one photodetector is imperative, especially when optimally slight differences in the ratio between the transmissions at the two wavelengths are to be detected. In practice, it is difficult to realize a system in which two detectors have (and maintain!) constant transfer characteristics throughout such a dynamic range. Consequently, the measurement at the two wavelengths will have to be performed sequentially and alternately. This is achieved by means of a butterfly shutter which, in spite of its being a moving, mechanical component, can be included in the arrangement in a relatively simple manner.

In the first embodiment the two types of light are derived from two separate light sources, each fed by an individual supply means. In connection with the requirements set, it is not feasible to derive both types of light from one source by filtering. There are no practical sources having a suitable line spectrum, while a continuous radiator is unable to concurrently satisfy the requirements as to absolute and relative stability in light output at both wavelengths, not even by means of an electric control. (When controlling the absolute light output the ratio at the two wavelengths will change, and vice versa.).

The source producing the measuring wavelength is chosen to be a mercury spectrum lamp. The double line at 577/579 nm in the mercury spectrum is highly suitable for hemoglobin detection at 578 nm. Such a narrow measuring spectrum increases the detection sensitivity due to the optimally great relative changes in transmission between a normal egg and a blood egg. The mercury double line can be readily filtered by means of an interference filter, there being no inconvenient background transmission of the filter in the rest of the spectrum, as there would have been when filtering a continuous spectrum. It is very well feasible to electronically stabilize the current of the mercury lamp of the type used. The reference wavelength is obtained by interference filtering of the continuous spectrum of a halogen lamp. By choosing a rather broad filter, variations in the spectral transmission of brown eggs are averaged. As a result thereof, the detection system is less sensitive to the steep curve of the spectrum of brown eggs at the reference wavelength. The light output of this lamp can be readily electronically varied, so that the ratio between the light outputs of the mercury and the halogen lamp can be controlled accurately. The simplest control is that in which the light output of the halogen lamp is made equal to that of the mercury lamp. In that case the ratio is accurately established and the absolute light output is determined by that of the current-stabilized mercury source.

FIG. 5 schematically shows the two light sources with the associated lens systems and servo loop circuit means for controlling the light output.

The light emitted by the two sources, i.e. mercury spectrum lamp 1 and halogen lamp 2, is converted by lenses 3 and 4 to substantially parallel beams which are filtered by interference filters 5 and 6 at 578 and 600 nm. After chopping by means of butterfly shutter 8 driven by D.C. motor 7, the beams are focused by lenses 9 and 10 at fibre optics 11, in which the beams are made to have the same optical axis. A small beam is branched-off from each input fibre beam 12, 13, which small beams are united at a detector 14. Another branched-off beam provides through detector 15 the synchronizing data from the rotating butterfly shutter. By means of a control signal circuit 16, included in the aforesaid servo loop circuit means and which has a phase locked loop configuration, control signals are derived from this data and applied to two measuring circuits 17 and 18 (sample and hold circuits). These two measuring circuits are controlled in counter phase, as a result of which the signal from detector 14 is synchronously sampled during the irradiation of the egg with light having wavelengths $\lambda_h$ and $\lambda_r$ respectively. The frequency of the butterfly shutter is now no longer critical. The samples from the signals obtained after the measurements at $\lambda_h$ and $\lambda_r$ respective are compared in a differential amplifier 19, which controls the halogen lamp as a control signal is applied to a controllable, stabilized voltage supply 20 used for feeding the halogen lamp 2. Lamp 1 is fed by a stabilized current source 21. A high closed loop gain ensures that the ratio between the two types of light reaching detector 14 (and, consequently, irradiating the egg) is maintained averagely constant (better than 0.1%). The bandwidth of the above control system for variations in the light output of the spectrum lamp is approximately 10 Hz. As a result thereof, for example, variations due to shuttling of the arc in the mercury lamp are compensated for in a sufficiently rapid manner.

The aim is to electro-optically candle five eggs per second. This implies that the measuring period available for each egg is approximately 100 msec. As during the (continuous) transport of the eggs in their transverse direction the transmission of an egg may vary, sufficient measurements must be performed at each wavelength in order to permit a fairly accurate measurement of the transmission ratio. For this reason a sampling frequency of 250 Hz is chosen, it being possible to take 25 samples at both wavelengths during the passage of an egg.

FIG. 6 shows a block diagram representing the electronic detection system in which the ratio between the transmissions at the respective wavelengths $\lambda_h$ and $\lambda_r$ is determined.

The light passed by egg 23 impinges upon a detector 22 including a silicon photodiode. Just as this is done for the lamp control, the data concerning the transmission of the egg at the two wavelengths could be derived from the output signal of this detector by means of two synchronous sample and hold circuits controlled in counter phase. Subsequently, only the ratio of the resultant signals, which are proportional to the transmissions at wavelengths $\lambda_r$ and $\lambda_h$ respectively, has to be determined. It is observed, however, that the absolute magnitude of the two signals has a dynamic range of 1:1000. It is rather difficult to construct circuitry able to determine ratios in a sufficiently rapid and accurate manner throughout such a range. Therefore, a solution has been looked for and found in the use of an automatic gain control.

Suppose the two transmissions occurring in the arrangement to be $T_r$ and $T_h$ respectively, and the voltages corresponding therewith and appearing at the output of the detector to be $V_r$ and $V_h$ respectively. In a control arrangement including a controllable amplifier 24, a differential amplifier 25 and sample-and-hold circuitry 26, each time during the measurement at $\lambda_r$, the gain A of amplifier 24 is controlled so that the voltage $V_r$ is given a fixed value $V_c$. The gain $A(V_r)$ will thus be $V_c/V_r$, so that $V_2 = (V_c/V_r) \cdot V_1$. Sample and hold circuitry 27, which is each time controlled during the measurement at $\lambda_h$, determines the value of $V_2$ occurring during a sample interval available for $\lambda_h$, let us say $V_3$. Then the following applies:

$$V_3 = A \cdot V_h \rightarrow V_3 = V_c \cdot (V_h/V_r).$$

After being passed through a low-pass filter 28, the signal voltage $V_3$ is compared in a comparator circuit 29 to a fraction $a$ of $V_c$ (voltage source 30), which represents the detection threshold.

A blood egg is concerned if:

$$V_3 = \frac{V_h}{V_r} \cdot V_c < aV_c \text{ or } \frac{V_h}{V_r} < a.$$

$a$ is set at approximately 0.6.

A constant deviation, if any, in the ratio between the light outputs of the two sources may be readily discounted in the factor $a$. The control circuit is capable of steering the voltage $V_r$ to $V_c$ within one sample (duration $\simeq$ 1.6 msec) at an accuracy of 0.2%. This control rate has the advantage that as many samples as possible can be utilized during the measuring period and that variations in the absolute transmission due to the transport of the eggs do not affect the determination of the transmission ratio. Consequently, the effective measuring period may be practically as long as the time of passage of an egg (100 msec), while low-pass filtering of the measuring signal $V_3$ is possible with a bandwidth of approximately 8 Hz.

FIG. 7 schematically shows a circuit arrangement adapted to control the detection threshold as a function of the transmission at wave length $\lambda_r$.

As appeared above, it would be desirable to have the possibility to influence the detection threshold as a function of the transmission at $\lambda_r$. To this end, signal $V_1$ from detector 22 is sampled in sample and hold circuitry 26 during the measurement at $\lambda_r$. The resultant voltage, which represents the absolute transmission at $\lambda_r$, is processed in processing circuitry (e.g. a log-converter). This circuitry controls the dependence of the detection threshold as a function of the transmission at $\lambda_r$. In this manner, at the same time the occurrence of old blood eggs having a very low absolute transmission can be detected. Signal $V_1$ is further analyzed in level detector 32, as a result whereof an egg transport synchronization signal is obtained at the output of 32, which signal is used to release circuitry 33 performing the ratio measurement and comparator 29 producing the decision signal. Noise produced by the detector and transients occuring in the AGC circuit will then have no influence on the initial condition of the low-pass filter used, so that $V_3$ will be independent of previous matters when an egg is measured.

The level detector will further indicate the absence of an egg on the conveyor, so that also in this event the entire circuit arrangement is reset. This has the additional advantage that an excessive light input due to such absence will not affect the measurement to the next successive egg.

FIG. 8 shows a number of measurement results achieved by means of an arrangement according to the present invention, which measurements are performed to a number of brown and white eggs, including some containing blood. Point A represents a rejected egg having a curdled yolk. Point B represents an egg having a blood spot of 2 mm in diameter. Point C represents an egg having three blood spots each of approximately 2 to 3 mm in diameter.

In the following and by making reference to FIGS. 9a, b and 10a–c respectively another embodiment of an automatic egg candling system will be described; with this embodiment the drawbacks discussed above and inherent to the embodiment described in the foregoing, can be eliminated.

The embodiment to be described in the following can be advantageously used with a conveying system wherein the eggs for inspection are lifted-off from the conveyor and are held sufficiently long, for instance 300 msec., in the light beam path for inspection, whereafter the respective egg is removed from that position and the following egg is lifted into the path of the optical beam etc. In the intermediate time interval between successive lift-offs, wherein no egg is present in the light beam path, the same photosensitive detector active during an "egg measurement interval", can be active to perform a light source measurement. With such basic arrangement the ultimate measurement of the desired ratio $T_h/T_r$ can be performed independently of the characteristics of the optical system. Variations in the transfer characteristics of this optical system and also variations at the locations at which the egg under inspection is placed in the optical beam path, have no influence on the results of the measurement, because such a variation in the optical system during the "light source measurement" and during the "egg measurement" as well, has the same influence on the ratio of the signals produced by the detector in response to light beam flashes with the different wavelengths $\lambda_h$ and $\lambda_r$. In the embodiment to be described in the following it is not necessary to employ a control system for regulating the light outputs of the light sources; as an additional advantage a single light source then can be employed for producing light beams having the different wavelengths $\lambda_h$ and $\lambda_r$, even in a conveying system with 12 parallelly running conveyor belts. With the embodiment to be described, actually from the signals proportional to $L_h$; $L_r$; $L_h \cdot T_h$ and $L_r \cdot T_r$ respectively, the ratio $T_h/T_r$ can be determined which means that the ratio of two sub-ratios will be determined.

Further a criterion has to be provided for the absolute transmission through an egg under inspection in order to offer the possibility to regulate the detection criterion. Such a criterion for the absolute transmission can be determined in a simple manner if the light output of the light sources would be regulated. The magnitude of the signals as developed by the photosensitive detector then is a criterion for such absolute transmission. However if an expensive and complicated source regulating system is not desired, an absolute criterion for the transmission $T_r$ at the wavelength $\lambda_r$ is to be found from signals $L_r$ and $L_rT_r$ by means of a measurement of the ratio thereof. A simple solution to that end will be also described in the following.

FIG. 10a shows a general diagram of an embodiment illustrative for an optical system to be employed in the automatic candling system. In the general diagram shown in FIG. 9a thereof, the optical system is depicted in the mid-column under the heading "optical" by reference-symbol 91. Although in the embodiment shown in FIG. 10a use is made of two separate light sources for alternately producing the different light beams with the wavelengths $\lambda_h$ and $\lambda_r$, it is also feasible to employ a single light source to that end. In FIG. 10a a light source 101 energized from a power supply-unit 102, by means of a mirror 103 and associated lenses 104 and 105 produces light which is tranmitted through an interference filter 106, along direction 1 and is focused on a disc 107 of a light chopper arrangement; said disc can be rotated by means of an associated drive motor 108. In a similar way light emitted from a light source 109 energized from a power supply unit 1010, by means of a mirror 1011 and associated lenses 1012 and 1013 respectively is transmitted through an interference filter 1014, is directed along optical axis 2 and focused on disc 107. Interference filter 106 selectively transmits light at the measurement wavelength $\lambda_h$, while interference filter 1014 selectively transmits light on the reference wavelength $\lambda_r$. FIG. 10b, more in particular lines 1 and 2, show the light beam intensities directed along axis 1 and 2 respectively and as focussed on disk 107. As shown in more detail in FIG. 10c the lower half of disc 107 has a light reflective surface, while the upper half of disc 107 is made of light transparent material. The dot shown at the left-hand portion of disc 107 in FIG. 10c is the point on which the beams along direction 1 and 2 are focused. Along optical axis 3, alternate light beam flashes with wavelengths $\lambda_r$ and $\lambda_h$ respectively are alternately provided as shown schematically in FIG. 10b line 3 thereof. By means of lenses 1015 and 1016 the light beam flahses which due to the light chopper action are thus alternately produced along direction 3, are focused on the input side of a fibre optic arrangement 1017. By means of this fibre optic arrangement it is possible to branch-off from light applied to its input, various sub-beams each leading to an associated measurement location. In a conveying system comprising twelve parallelly running conveyor belts, it is for instance possible to branch-off six sub-beams from the direction 3, while also branching-off six sub-beams from light directed along the direction 4, along which direction also the wave length $\lambda_r$ and $\lambda_h$ are alternately provided as illustrated in FIG. 10b line 4. Each one of these sub-beams branched-off from the fibre optic arrangement such as 1017 is used for the alternate performance of a "light source measurement" and a "egg measurement" respectively. Actually with the organization described in the fore-going a double sequential measurement system is provided. Not only light beam flashes with the wavelengths $\lambda_h$ and $\lambda_r$ are alternately produced, but also the light source measurement and the egg measurement are alternately performed. This is also schematically illustrated in the waveform diagram shown in FIG. 9b with waveforms indicative of the operation of the general block diagram shown in FIG. 9a. At the output side of each one of the afore-mentioned sub-beams branched-off of the fibre optic arrangement 1017, an egg inspection (or egg measurement) location has been provided such as has been schematically illustrated in FIG. 10a by the position 1018. An opto-electronic detector, or a photosensitive detector 1019 such as for instance a photodiode, is effective to convert the light beam flashes applied thereto into corresponding electric signals. Between the egg inspection position and the input side of said photosensitive detector, a diaphragm 1020 has been provided. By 1020' the front surface of the diaphragm has been shown. During an egg measurement time interval, the upper aperture is between the egg under inspection and the input side of the photosensitive detector, while during a light source measurement interval the diagram is shifted so as to present a small aperture between the egg under inspection and the input side of the photosensitive detector. The diameter of the small aperture has been selected in a manner so as to avoid over exposure from the light beam flashes produced at the output side of the fibre optic arrangement, in the absence of an egg at the measurement location. The time available between the removal of an egg from the measurement position and the replacement of a subsequent egg thereat, can also effectively used for performing an automatic offset-compensation of the electrical detection arrangement to eliminate drift as for instance caused by temperature effects. Therefore the afore-mentioned photosensitive detector is also effectively closed off for environmental light during the time interval between a light source measurement and an egg measurement. Along the periphery of the light chopper disc 107, also a slotted optical switch 1021 has been provided from which control signals for the electric detection arrangement to be described hereinafter are derived.

With reference to FIGS. 9a and 9b the over all detection system and associated controls will now be described. As has been shown schematically in FIG. 9a this system can be divided in a mechanical portion, an optical portion and an electrical portion. The optical system as described in the foregoing is indicated in FIG. 9a by the general block 91 and comprises a light emitting arrangement 92; a light chopper arrangement 93; a fibre optic arrangement 94; an egg measurement station 95; a diaphragm 96 and a photosensitive detector 97. The slotted optical switch 98 associated with the light chopper arrangement 93 and a voltage controlled drive motor 99 for the light chopper disc are also indicated in FIG. 9a. All these elements have been discussed more in detail in the foregoing description of FIG. 10a–c. The over all detection system is synchronously controlled from the band transport mechanism 910 and by means of another light chopper arrangement 911 and associated slotted optical switch 912 the necessary information regarding the progress or phase of a complete egg inspection cycle can be derived.

As shown schematically in FIG. 9b such a complete egg inspection cycle is initiated with an offset-compensation interval for the electrical detection arrangement, which offset-compensation is performed when the egg previously inspected is removed. Following the offset-compensation, a source measurement is performed, when the respective egg has been removed from the light beam path extending through the egg measurement position. Following the source measurement time interval again an offset-compensation is performed during the time interval that a subsequent egg for inspection is lifted-off from the conveyor into the measurement position. Following this last offset-compensation interval, the actual egg measurement is performed. In practice the frequency of the source measurement and the offset-compensation as well, can be decreased to a certain extent; however due to the structure of the egg lift-off mechanism 913 the time interval available for an egg measurement is limited to a fraction of about 3/10 to 4/10 of the complete egg inspection cycle. The remaining 7/10 to 6/10 portion of such an egg inspection cycle is then effectively available for an accurate source measurement and offset-compensation. The light chopper arrangement 93 is included in a first phase locked loop circuit arrangement by means of which said light chopper is synchronously coupled to the band transport mechanism 910 in such manner that each inspection cycle is always initiated with the same type of light beam flash, for instance a flash including the reference wavelength $\lambda_r$. This first phase locked loop 914 comprises a phase detector with an associated loop filter 915 and the voltage controlled drive motor 99 for driving the light chopper arrangement 93. The information regarding the phase position of said chopper can be derived by means of the slotted optical switch 98 which corresponds to the slotted optical switch 1021 shown in FIG. 10a. As will become clear from the wave form diagrams shown in FIG. 9b in combination with the block diagram of FIG. 9a, wherein the dotted line segments at the right side thereof correspond with the dotted line segments at the left-side of FIG. 9b, information regarding the phase position of the transport mechanism 910 is derived by means of the light chopper arrangement 911 and associated slotted optical switch 912 which at its output delivers set and reset signals respectively for a digital selection circuit 916. The electrical signals delivered by said optical switch 912 are shown in FIG. 9b on the lines indicated by "moving band phase" and "light chopper signal" respectively. The output signals delivered by the digital selection circuit 916 are shown in FIG. 9b on the lines indicated by the legends "offset-compensation", "source measurement" and "egg measurement" respectively.

The actual measurements have to be performed in response to light beam flashes of the wavelengths $\lambda_r$ and $\lambda_h$. Due to the finite dimensions of the focused light spot on the light chopper disc, the rise time of the light beam flashes as produced by the light chopper arrangement 93 and indicated in FIG. 9b by the wave form with the legend "wavelength of light", has a finite value, i.e. different from zero. Therefore the electric command signals dictating the execution of the source measurement and the egg measurement are required to fall within the time intervals defined by the light beam signals derived from said light chopper arrangement 93. To that end a second phase locked loop 917 is employed. This phase locked loop circuit 917 comprises a voltage controlled clock oscillator 918, which at its output delivers clock pulses indicated in FIG. 9b by the waveform with the legend "clock". These clockpulses are synchronously coupled to the light chopper arrangement 93 through a phase detector with associated loop filter 919 also included in the phase locked loop circuit 917. By means of a digital selection circuit 920 electrical pulses are derived, indicated in FIG. 9b by the wave forms with the legends "$\lambda_h$ sampling" and "$\lambda_r$ sampling" respectively from which by means of a further digital selection circuit 921 the electrical command signals defining the respective time intervals for the execution of a source measurement and an egg measurement, are derived. These command signals are shown in FIG. 9b by the wave forms with the legends "$\lambda_h$ source sampling" and "$\lambda_h$ egg sampling" respectively. Together with the command signals "$\lambda_r$ sampling"; "moving band phase", and "offset compensation" respectively, these command signals are employed to control the operation of the electrical detection arrangement 922 which will be described more in detail with reference to FIG. 11. At this time it will be noted that the electrical detection arrangement 922 is adapted to produce a reject signal if an egg under inspection contains a certain amount of blood. Such reject signal through a delay circuit 923 can operate an egg reject mechanism 924 by means of which the respective blood egg can be sorted out. Further the mechanical portion of the over all detection system comprises a diaphragm control arrangement 925 for controlling the movement of the diaphragm 96 in the manner as discussed in relation to FIG. 10a. The control actions performed by the control arrangement 925 are derived from the signals "source measurement" and "egg measurement" respectively (FIG. 9b) as derived by the digital selection circuit 916.

FIG. 11 shows a block diagram of an embodiment illustrative for the electrical detection arrangement shown in FIG. 9a and by means of which the desired ratio measurements are performed. In the description of the operation of the embodiment shown in FIG. 11 it is assumed that an egg measurement directly follows a source measurement; the offset-compensation will not further be dealt with because this aspect is not part of the invention and is moreover generally known in the art. As already pointed out in the foregoing, the desired ratio $T_h/T_r$ has to be derived from the available voltages $V_r$ and $V_h$ respectively proportional to the light beam flashes $L_r$ and $L_h$ produced by the optical system in the absence of an egg in front of the photosensitive detector, and the signals $V_r \cdot T_r$ and $V_h \cdot T_h$ respectively which are proportional to the light transmitted ($L_r \cdot T_r$ and $L_h \cdot T_h$ respectively) through an egg under inspection. It has to be kept in mind that the absolute magnitude of the signals can vary within a dynamic range of 1:1000. In practice it is difficult to design dividing circuits capable of determining ratios with sufficient speed and accuracy over such wide a dynamic range. The solution offered by this invention has been found in the employment of a controllable gain amplifier. FIG. 11 is illustrative of such a solution wherein use is made of a controllable gain amplifier.

The associated wave form diagrams depicted at the right-hand side in FIG. 11 are illustrative of the various light beam flashes and corresponding electrical signals with associated electrical command signals, involved in the operation of the electrical detection arrangement.

Figure 10:
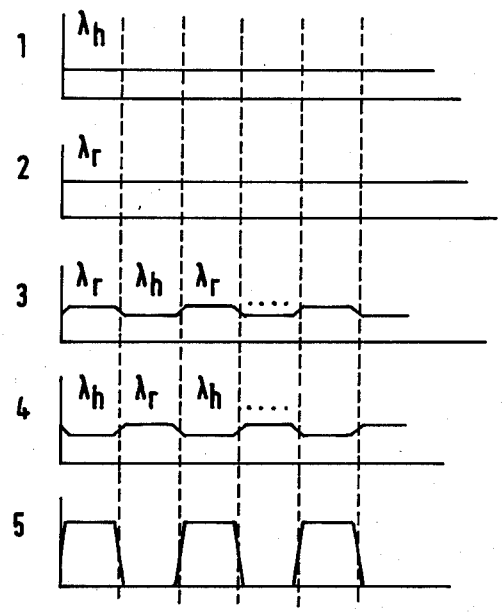
Figure 10:
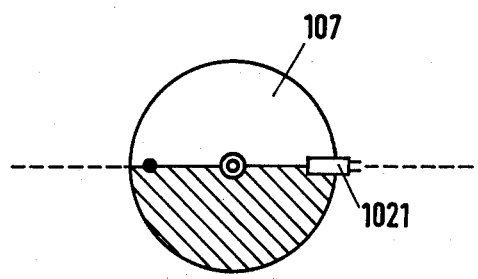

In FIG. 11 the optical system 111 alternately produces the light beam flashes generally indicated by $L_1$ and as discussed in connection with the foregoing FIGS. 9 and 10 respectively, along an optical axis on which an egg 112 under inspection can be placed, on photosensitive detector 113. An egg placed in the light beam path has a transmission $T_h$ and $T_r$ respectively for light beam flashes at the wavelength $\lambda_h$ and $\lambda_r$ respectively. The light beam flashes developed at the output of the optical system are indicated by the waveforms indicated in FIG. 11 by $L_1$. In a similar way the light beam flashes after having been transmitted through the egg under inspection and as applied to the input of the photosensitive detector are indicated by the wave forms $L_2$. The corresponding electrical voltages $V_1$ are produced at the output of the detector 113 and are indicated schematically by the wave forms $V_1$. These voltages are applied to the input of a controllable gain amplifier 114. The output signal generally indicated by $V_2$ of said amplifier 114 is applied to the one input terminal of a differential amplifier 115, the input of a sample and hold circuit 116 and the input of an other sample and hold circuit 117. The other input of the differential amplifier 115 is connected to a fixed reference voltage $V_C$. Said differential amplifier 115 with a further sample and hold circuit 118 connected at its output provides a control loop for regulating the gain of the amplifier 114 in such a manner that during the time intervals in which the optical system 111 delivers light beam flashes at the reference wavelength $\lambda_r$, the amplifier gain A is regulated in such a manner that the corresponding electrical voltage $V_r$ delivered at the output of the photosensitive detector 113 in the respective time interval is brought on a fixed value $V_C$ at the output of amplifier 114. In other words the gain $A_{source}$ in this situation is given by $V_C/V_r$. With the gain thus adjusted and sample and hold circuit 116 activated by the command signals occurring during the $\lambda_h$-time intervals of a source measurement time interval, the output signal $V_1$ of the photosensitive detector arrangement is measured. The result of such measurement is a voltage $V_3$ delivered of the output of said sample and hold circuit 116 given by:

$$V_3 = A_{source} \cdot V_h = \frac{V_C}{V_r} \cdot V_h = V_C \cdot \frac{V_h}{V_r}$$

With this voltage a criterion now has been given for the ratio between the light output of the optical system at the measurement wavelength $\lambda_h$ and the light output of said optical system at the reference wavelength $\lambda_r$. Subsequently the same control circuit is employed for the actual egg measurement during the respective egg measurement interval. During that phase of the complete egg inspection cycle the control loop again is effective to regulate the gain A of said amplifier 114 in such a manner that the input voltage $V_r \cdot T_r$ applied thereto in the respective $\lambda_r$ time interval of the egg measurement time interval is brought on the fixed value $V_C$. The gain thus adjusted is then given by $A_{egg} = V_C/V_r T_r$. With the gain thus adjusted and the sample and hold circuit 117 activated by the command signals occurring during the respective $\lambda_h$ time intervals of the egg measurement time interval, at the output of said sample and hold circuit 117 a voltage $V_4$ is delivered given by:

$$V_4 = A_{egg} V_h T_h = \frac{V_C}{V_r T_r} \cdot V_h T_h = V_C \cdot \frac{V_h}{V_r} \cdot \frac{T_h}{T_r}$$

Thus the voltage $V_4$ is a criterion for the ratio between the amount of light delivered after transmission through the egg under inspection at the measurement wavelength $\lambda_h$ and the amount of light delivered after transmission through the egg under inspection at the reference wavelength $\lambda_r$.

Assuming that the detection threshold $T_h/T_r$ is set at a definite value $a$, following relations exist:

for eggs to be approved $T_h/T_r > a$; eggs to be rejected (blood eggs) $T_h/T_r < a$. Consequently with the foregoing arrangement a comparator for comparing a voltage $V_5 = aV_3$ and the voltage $V_4$, can be employed for determining whether or not an egg under inspection has to be rejected. The comparison performed by comparator 119 can be described as follows:

$$V_4 > V_5 \longrightarrow V_C \frac{V_h T_h}{V_r T_r} > a V_C \frac{V_h}{V_r} \longrightarrow$$

$$\frac{T_h}{T_r} > a \longrightarrow \text{egg approved}$$

$$V_4 < V_5 \longrightarrow \frac{T_h}{T_r} < a \longrightarrow \text{egg rejected.}$$

The decision signal as developed at the output of comparator 119 is delayed to such extent that the egg to be rejected has reached a position where it can be sorted out by the reject mechanism.

As already has been discussed in the foregoing it is of importance that the detection threshold $a$ can be controlled as a function of the transmission $T_r$ of an egg under inspection at the reference wavelength $\lambda_r$.

In connection with this desired facility the controllable gain amplifier is of the type wherein the gain is an exponential function of the gain control voltage $V_g$. In other words $A = e^{\gamma V_g}$. The ratio between the gain adjusted during a source measurement interval and the gain adjusted during an egg measurement interval is given by:

$$\frac{A_{egg}}{A_{source}} = \frac{\frac{V_C}{V_r T_r}}{\frac{V_C}{V_r}} = T_r \text{ and thus equals } e^{\gamma \delta V_g},$$

wherein $\delta V_g$ represents the difference of the gain control voltages necessary to adjust the gain during the source measurement interval and the egg measurement interval. In other words $\delta V_g$ is proportional to the logarithm of $T_r$. Consequently $\delta V_g$ is a magnitude which is particularly suitable for controlling the detection threshold $a$. (Compare e.g. foregoing FIG. 4b wherein the detection threshold is represented by a straight line in a graphical representation wherein $T_r$ is indicated along a logarithmic axis. A person skilled in the art can easily design various embodiments in which the detection threshold $a$ can be controlled in the above-indicated manner.

FIG. 8 is illustrative of results obtained with an egg candling system of the subject invention. A straight line indicative for a ratio $T_h/T_r = 0.61$ separates the rejected eggs from the approved eggs, even without control of the detection threshold as a function of $T_r$.

As already observed the invention is not restricted to the described automatic egg candling system. The invention can also be employed in those cases wherein the relevant information is related to selective absorption.

We claim:

1. A detection system for automatically detecting a first light transmissive substance in a second and different light transmissive substance, comprising light emitting means for alternately producing light beam flashes of light having a first wavelength and light having a second wavelength; support means for temporarily supporting a volume containing said first and said second substance respectively in the light beam path; optoelectric detecting means for converting light beam flashes directed along said light beam path into corresponding electrical voltages; an electrical detecting arrangement comprising means for producing a first voltage proportional to the ratio between light transmitted through said volume under inspection at said first wave-length and light transmitted through said volume under inspection at said second wave-length, and means for producing a second voltage proportional to the product of a detection threshold and the quotient of light transmitted directly (in the absence of said volume in front of said opto-electrical detector) to said opto-electric detecting means at said first wavelength and light directly transmitted to said opto-electric detecting means at said second wavelength; and comparator means for comparing said first voltage and said second voltage for providing a decision signal indicating whether or not the ratio between the transmission through said volume under inspection at said first wavelength and the transmission through said volume at said second wavelength exceeds said detection threshold.

2. A detection system in accordance to claim 1 wherein said means for producing said first voltage comprises a sample and hold circuit which is selectively activated during time intervals at which lght beam flashes at said first wavelength are transmitted through said volume under inspection; said means for producing said second voltage comprises another sample and hold circuit which is selectively activated during time intervals corresponding to light beam flashes which at said first wavelength are transmitted directly to said opto-electric detecting means.

3. A detection system in accordanc to claim 1 wherein said electric detection arrangement comprises a controllable gain amplifier with a control input through which its gain is controlled in dependence of a gain control signal, a control loop circuit for deriving said gain control signal from voltages corresponding to light beam flashes which at said second wavelength are transmitted directly (in the absence of said volume in front of the opto-electric detecting means) to said opto-electric detecting means and including comparator means for regulating said gain in such a manner that in response to said light beam flashes which at said second wavelength are directly applied to said opto-electric detecting means, a constant voltage corresponding to a reference voltage is produced at the output of said amplifier.

4. A detection system in accordance to claim 1 wherein said light emitting means comprises a fibre optic arrangement for receiving at its input side the alternately produced light beam flashes with light of said first wavelength and light of said second wave length and having one or more output ends for a corresponding number of measurement locations.

5. A detection system in accordance with claim 4 wherein said light emitting means comprises a light chopper arrangement for alternately applying light with said first wavelength and light with said second wavelength to said input side of said fibre optic arrangement.

6. A detection system in accordance with claim 5 wherein said light emitting means comprises a single light source producing light containing said first wavelength and said second wavelength as well.

7. A detection system in accordance with claim 5 wherein an optical switch is associated with said light chopper arrangement in such a manner that command signals for the activation of said electric detection arrangement are derived from the output of said optical switch.

8. A detection system for automatically detecting a first light transmissive substance in a second and different light transmissive substance, comprising: light emitting means for alternately producing light beam flashes of light having a first wavelength and light having a second wavelength; support means for temporarily supporting a volume containing said first and said second substance respectively in the light beam path; opto-electric detecting means for converting light beam flashes directed along said light beam path into corresponding electric voltages; an electric detecting arrangement comprising a controllable gain amplifier with a control input through which its gain is controlled in dependence of a gain control signal, a control loop circuit for deriving said gain control signal from voltages corresponding to light beam flashes which at said second wavelength are transmitted directly (in the absence of said volume in front of the opto-electric detecting means) to said opto-electric detecting means and including comparator means for regulating said gain in such a manner that in response to said light beam flashes which at said second wavelength are directly applied to said opto-electric detecting means, a constant voltage corresponding to a reference voltage is produced at the output of said amplifier, a sample and hold circuit which is selectively activated during time intervals at which light beam flashes at said first wavelength are transmitted through said volume under inspection, in order to produce a first voltage proportional to the ratio between light transmitted through said volume under inspection at said first wavelength and light transmitted through said volume under inspection at said second wavelength, and another sample and hold circuit which is selectively activated during time intervals corresponding to light beam flashes which at said first wavelength are transmitted directly to said opto-electric detection means, so as to produce a second voltage proportional to the product of a detection threshold and the quotient of light transmitted directly to said opto-electric detecting means at said first wavelength and light directly transmitted to said opto-electric detecting means at said second wavelength; and comparator means for comparing said first voltage and said second voltage for providing a decision signal indicating whether or not the ratio between the transmission through said volume under inspection at said first wavelength and the transmission through said volume at said second wavelength exceeds said detection threshold.

9. A detection system for automatically detecting a first light transmissive substance in a second and different light transmissive substance, comprising light emitting means for alternately producing light beam flashes of light having a first wavelength and light having a second wavelength; support means for temporarily supporting a volume containing said first and said second substance respectively in the light beam path; opto-electric detecting means for converting light beam flashes directed along said light beam path into corresponding electric voltages; an electric detecting arrangement comprising means for producing a first voltage proportional to the ratio between light transmitted through said volume under inspection at said first wavelength and light transmitted through said volume under inspection at said second wavelength, and means for producing a second voltage proportional to the product of a detection threshold and the quotient of light transmitted directly to said opto-electric detecting means at said first wavelength and light directly transmitted to said opto-electric detecting means at said second wavelength, and a controllable gain amplifier with a control input through which its gain is controlled independence of a gain control signal, a control loop circuit for deriving said gain control signal from voltages corresponding to light beam flashes which at said second wavelength are transmitted directly and through said volume under inspection as well to said opto-electric detecting means and including comparator means for regulating said gain in such a manner that in response to said light beam flashes which at said second wavelength are applied to said opto-electric detecting means, a constant voltage corresponding to a reference voltage is produced at the output of said amplifier, said comparator means for regulating the gain of said controllable gain amplifier comprises a sample and hold circuit which is selectively activated during time intervals corresponding to light beam flashes at said first wavelength; and further comparator means for comparing said first voltage and said second voltage for providing a decision signal indicating whether or not the ratio between the transmission through said volume under inspection at said first wavelength and each transmission through said volume at said second wavelength exceeds said detection threshold.

10. A detection system in accordance to claim 9, wherein said means for producing said first voltage comprises a sample and hold circuit which is selectively activated during time intervals at which light beam flashes at said first wavelength are transmitted through said volume under inspection; said means for producing said second voltage comprises another sample and hold circuit which is selectively activated during time intervals corresponding to light beam flashes which at said first wavelength are transmitted directly to said opto-electric detecting means.

* * * * *

UNITED STATES PATENT AND TRADEMARK OFFICE
CERTIFICATE OF CORRECTION

PATENT NO. : 4,063,822
DATED : December 20, 1977
INVENTOR(S) : Leendert Pieter deJong and Jan Davidse It is certified that error appears in the above–identified patent and that said Letters Patent are hereby corrected as shown below:

Column 1, line 28: "slectively" should be --selectively--;

Column 1, line 47: "light" should be --lights--;

Column 1, line 60: "object" (second occurrence) should be --subject--;

Column 2, line 39: "$L_n/L_r$" should be --$L_h/L_r$--;

Column 3, line 4: "detrementally" should be --detrimentally--;

Column 3, line 8: "system should be --systems--;

Column 3, line 22: "off" should be --of--;

Column 3, line 25: "ligh" should be --light--;

Column 4, line 7: "$T_n/T_r > a$" should be --$T_h/T_r > a$--;

Column 4, line 54: "optical" should be --optimal--;

Column 5, line 30: "an" should be --and--;

Column 5, line 39: "in sufficient" should be --insufficient--;

Column 6, line 3: "$\lambda_n$" should be --$\lambda_h$--;

Column 6, line 6: "1,6" should be --1.6--;

Column 6, line 23: after "optimal" insert --choice--;

UNITED STATES PATENT AND TRADEMARK OFFICE
CERTIFICATE OF CORRECTION

PATENT NO. : 4,063,822
DATED : December 20, 1977
INVENTOR(S) : Leendert Pieter deJong and Jan Davidse It is certified that error appears in the above-identified patent and that said Letters Patent are hereby corrected as shown below:

Column 6, line 26: "$\lambda_r (T\lambda_h/t\lambda_h)$" should be -- $\lambda_r (T\lambda_h/T\lambda_r)$ --;

Column 6, line 31: "responsive" should be --respective--;

Column 6, line 53: "$\lambda_h \simeq 600nm$" should be -- $\lambda_r \simeq 600nm$ --;

Column 8, line 33: "respective" should be --respectively--;

Column 8, line 43: "10 Hz" should be --100 Hz--;

Column 9, line 26: "fraction a" should be --fraction $\underline{a}$--;

Column 9, line 30: "$V_3 = \frac{V_h}{V_r} \cdot V_c < aV_c$ or $\frac{V_h}{V_r} < a$" should be -- $V_3 = \frac{V_h}{V_r} \cdot V_c < \underline{a}V_c$ or $\frac{V_h}{V_r} < \underline{a}$ --;

Column 9, line 33: "a" should be --$\underline{a}$--;

Column 9, line 36: "a" should be --$\underline{a}$--;

Column 9, line 57: after "circuitry" insert --31--;

Column 9, line 68: "occuring" should be --occurring--;

UNITED STATES PATENT AND TRADEMARK OFFICE
CERTIFICATE OF CORRECTION

PATENT NO. : 4,063,822
DATED : December 20, 1977
INVENTOR(S) : Leendert Pieter deJong and Jan Davidse It is certified that error appears in the above-identified patent and that said Letters Patent are hereby corrected as shown below:

Column 10, line 41: "locations" should be --location--;

Column 11, line 19: "tranmitted" should be --transmitted--;

Column 11, line 42: "flahses" should be --flashes--;

Column 11, line 59: "fore-going" should be --foregoing--;

Column 12, line 18: "over exposure" should be --overexposure--;

Column 13, lines 49-50: "measurement" (two occurrences) should be --measurements--;

Column 14, line 17: "diagram" should be --diaphragm--;

Column 15, line 6 : "an other" should be --another--;

Column 16, line 16: in "threshold a" - the "a" should have been typed in italics to distinguish it as being a component of the equation;

UNITED STATES PATENT AND TRADEMARK OFFICE
CERTIFICATE OF CORRECTION

PATENT NO. : 4,063,822
DATED : December 20, 1977
INVENTOR(S) : Leendert Pieter deJong and Jan Davidse It is certified that error appears in the above-identified patent and that said Letters Patent are hereby corrected as shown below:

Column 17, line 20 (Claim 2):  "lght" should be --light--;

Column 17, line 28 (Claim 3):  "accordanc" should be --accordance--;

Column 19, line 1 (Claim 9):  "independence" should be --in dependence--.

Signed and Sealed this

Twentieth Day of June 1978

[SEAL]

Attest:

RUTH C. MASON
Attesting Officer

DONALD W. BANNER
Commissioner of Patents and Trademarks